(12) United States Patent
Lo

(10) Patent No.: US 6,582,407 B1
(45) Date of Patent: Jun. 24, 2003

(54) STRUCTURAL SAFETY DESIGN FOR THE PREVENTION OF MIS-PRESSING PLUNGER ROD INTO SYRINGE

(75) Inventor: Pi-Chang Lo, Taoyuan (TW)

(73) Assignee: M.K. Meditech Co., Ltd., Taoyuan (TW)

( * ) Notice: Subject to any disclaimer, the term of this patent is extended or adjusted under 35 U.S.C. 154(b) by 0 days.

(21) Appl. No.: 10/219,306

(22) Filed: Aug. 16, 2002

(51) Int. Cl.7 .......................... A61M 5/315; A61M 5/00
(52) U.S. Cl. ........................................ 604/220; 604/110
(58) Field of Search ................................ 604/218, 220, 604/187, 208, 210, 235, 110

(56) References Cited

U.S. PATENT DOCUMENTS

| | | | | |
|---|---|---|---|---|
| 4,386,606 A | * | 6/1983 | Tretinyak et al. | 604/220 |
| 4,744,791 A | * | 5/1988 | Egolf | 604/229 |
| 5,067,948 A | * | 11/1991 | Haber et al. | 604/213 |
| 5,263,934 A | * | 11/1993 | Haak | 604/110 |
| 5,312,348 A | * | 5/1994 | Sans | 604/110 |
| 5,651,372 A | * | 7/1997 | Caillouette | 128/753 |
| 5,803,918 A | * | 9/1998 | Vetter et al. | 604/110 |
| 5,931,813 A | * | 8/1999 | Liu | 604/110 |
| 6,371,941 B1 | * | 4/2002 | Kato et al. | 604/220 |

* cited by examiner

Primary Examiner—Sharon Kennedy

(57) ABSTRACT

A structural safety design for the prevention of mis-pressing plunger rod into syringe mainly designs for single-used syringes, of which set a locking socket and a safety locking tab at the plunger rod end. An obstruction is formed between the plunger rod and the flange of hollow fluid chamber before the safety locking tab is pressed into the locking socket, so that the plunger rod can not be thoroughly pressed into the hollow cylinger. The invention, therefore, provides with a safety structure that effectively prevents from the unable-to-use problem of a syringe resulting from the plunger rod is mis-pressed into the hollow cylinder engaging with other components inside before the fresh syringe being used.

3 Claims, 7 Drawing Sheets

STRUCTURAL SAFETY DESIGN FOR THE PREVENTION OF MIS-PRESSING PLUNGER ROD INTO SYRINGE

BACKGROUND OF THE INVENTION (A) Field of Invention

The present invention relates to a structural safety design for the prevention of mis-pressing a plunder rod into a syringe, specifically, the invention proposes a required safety design for a compulsive single-used syringe structure to prevent mis-press of plunger before being used from unworkable syringe, due to the earlier engagement of the unused syringe with other peripheral components thereof. The invention enables a locking socket and a safety locking tab set at the end of the plunger rod to be anchored with each other by a corresponding groove and a corresponding protrusion thereof, respectively; therefore, a user, before carrying out the injection, has to press the safety locking tab into the locking socket to enable complete application of pressing the plunger rod into the distal(front) end of the syringe cylinder.

(B) Description of Prior Art

Iatrogenic infection is a critical problem that can not be disregarded and the infection source of most fatal diseases is through blood, therefore, the requirements for making single-used medical apparatuses become important developments. For instance, many self-destructed injector cylinders are to prevent from syringe being used twice.

Presently known self-destructed syringe designs mainly enable the syringe destruction by way of the plunger rod being pressed into the distal(front) end of the syringe cylinder, where self-destruction ways of syringes include destroying plunger, cylinder, needle structure, rubber stopper, etc., so that a self-destructed syringe can no longer be used when the plunger rod is pressed into the distal(front) end of the cylinder, i.e., one-time usage. However, the kind of self-destructed syringe design constantly results in unnecessary loss or waste owing to frequent syringe destruction during the processes of syringe assemblies and deliveries, or the mis-press of syringes by related hospital specialists.

In view of the foregoing, the prevention of mis-pressing plunger rod of self-destructed syringe has become a focus concern and the inventor aims at resolving the aforementioned drawbacks to install a safety apparatus on self-destructed syringes for decreasing the syringe defect rates during assembly and preventing the syringe delivery or improper usage by hospital specialists from possible losses.

SUMMARY OF THE INVENTION

The invention, a structural safety design for the prevention of mis-pressing plunger rod into syringe that effectively reduces improper, self-destruction of syringe, mainly sets a locking socket and a safety locking tab at the plunger rod end for corresponding connection with each other. A prior movement by pressing the safety locking tab into the locking socket has to be made before the plunger rod of syringe can be completely pressed into the distal(front) end of the cylinder for injection.

To enable a further understanding of the objective, structural features and function of the present invention, the detailed descriptions of the preferred embodiments are followed by the brief descriptions of the drawings below.

DETAILED DESCRIPTION OF THE PREFERRED EMBODIMENTS

Figure 1:
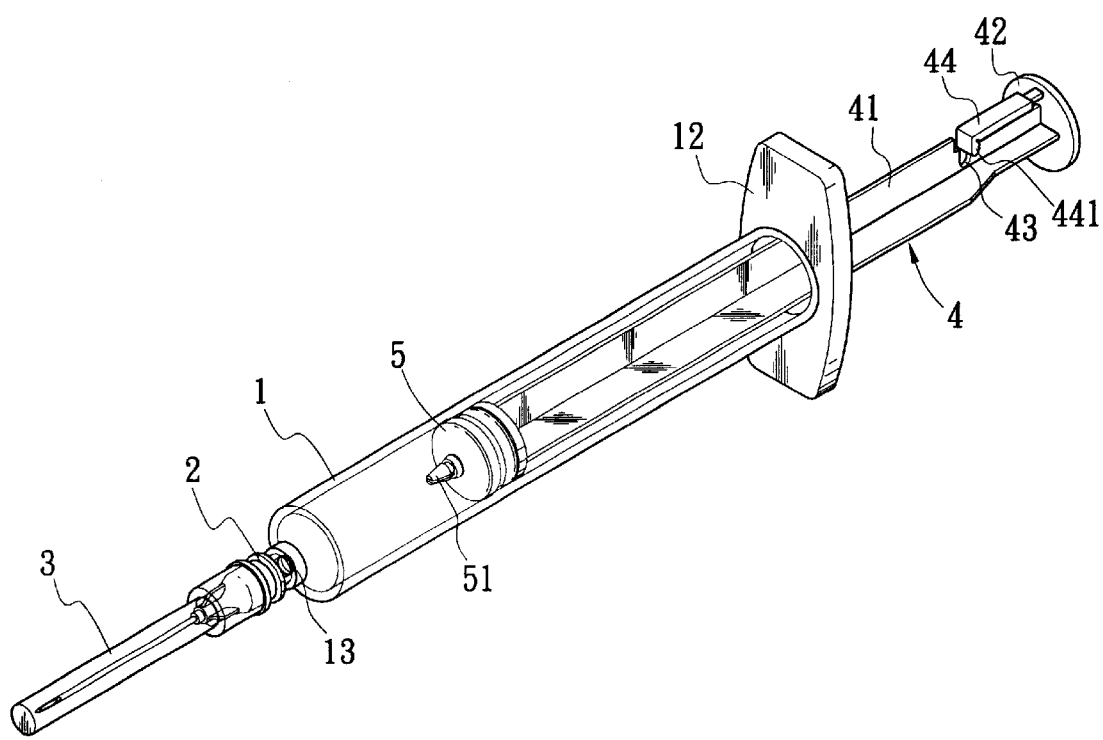
FIG. 1 is a perspective assembly diagram of a self-destructed syringe according to the invention.
Figure 2:
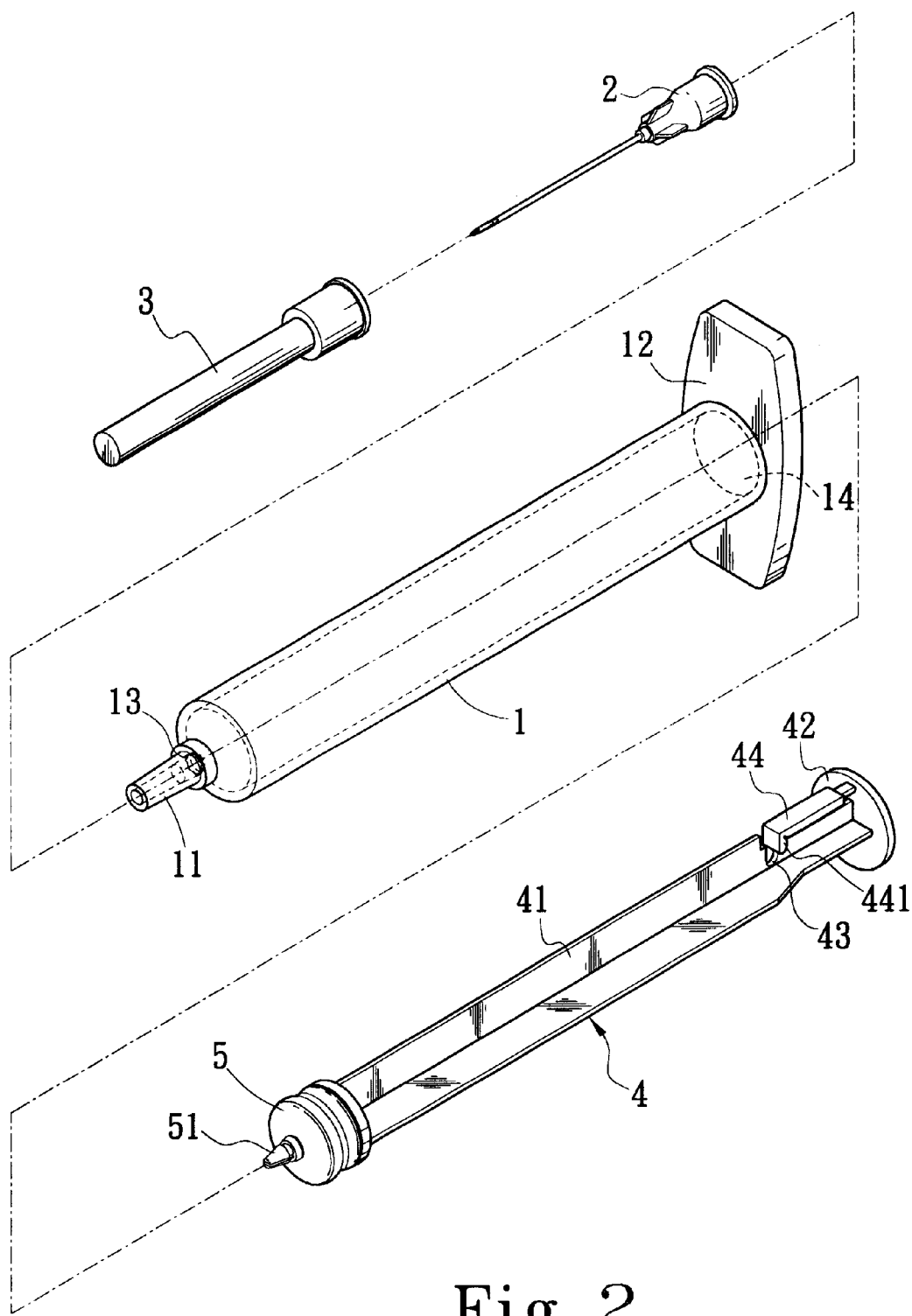
FIG. 2 is an exploded structural diagram of the self-destructed syringe according to the invention.

FIGS. 1 and 2 respectively show the perspective assembly diagram of a self-destructed syringe and the exploded structural diagram thereof. As shown in the drawings that the self-destructed syringe structure mainly consists of a hollow cylinder 1, a needle structure 2, a tip protector 3, a plunger rod 4, and a rubber stopper 5, wherein at the front end of the hollow cylinder 1 forms an indented connection head 11 for fixing the needle 2, which is outwardly covered by the tip protector 3. The syringe sets a buckle 13 inside the connection head 11 of the syringe cylinder enabling a conical portion 51 at the front end of the plunger rod 4 to be fully engaged in the connection head 11 resulting in syringe self-destruction, while the plunger rod 4 is completely pressed into the distal(front) end of the syringe cylinder.

The syringe sets a thumb rest 12 at the rear end of the hollow cylinder 1. A hollow fluid chamber 14 accommodates the plunger rod 4, which comprises a plurality of sectorial blades 41 extending from the front end to the thumb rest 42.

The air-tight condition that is formed between the conical portion 51 at the front end of the plunger rod 4 and the hollow fluid chamber 14 enables the plunger rod 4 to make piston movements back and forth for extracting or injecting medical pharmaceuticals.

The invention, a structural safety design for the prevention of mis-pressing plunger into syringe that effectively reduces improper self-destruction of syringe, mainly sets a locking socket 43 and a safety locking tab 44 at one of sectorial blades 41 of the plunger rod 4 near the thumb rest 42, where the safety locking tab 44 is in L shape and forms a head 441, which is corresponding to and can be embedded into the locking socket 43.

Figure 3A:
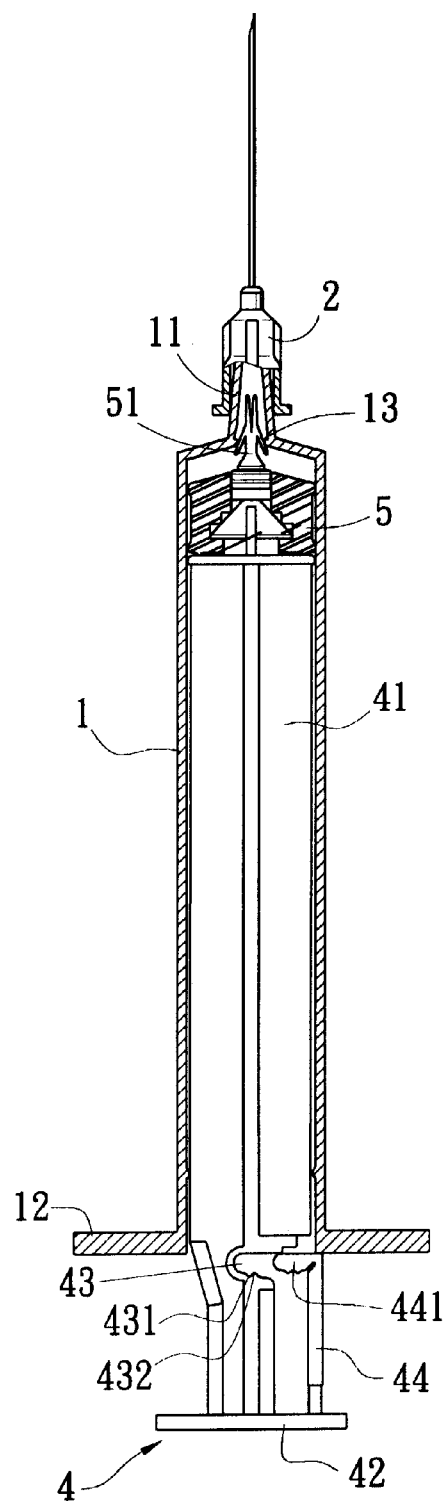
FIG. 3A is a preferred embodiment of sectional diagram of the self-destructed syringe according to the invention.
Figure 3B:
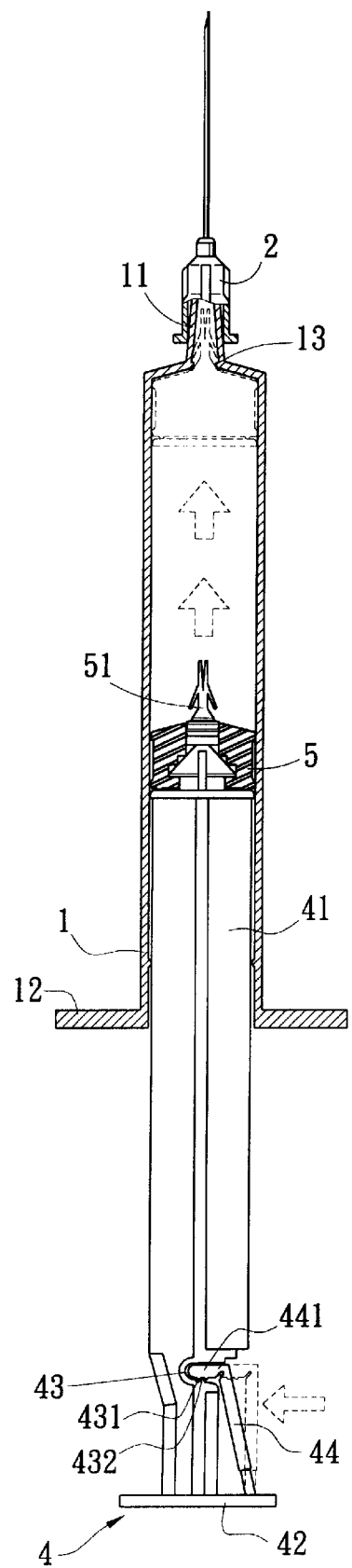
FIG. 3B is a schematic diagram illustrating the use of the self-destructed syringe according to the invention.
Figure 3C:
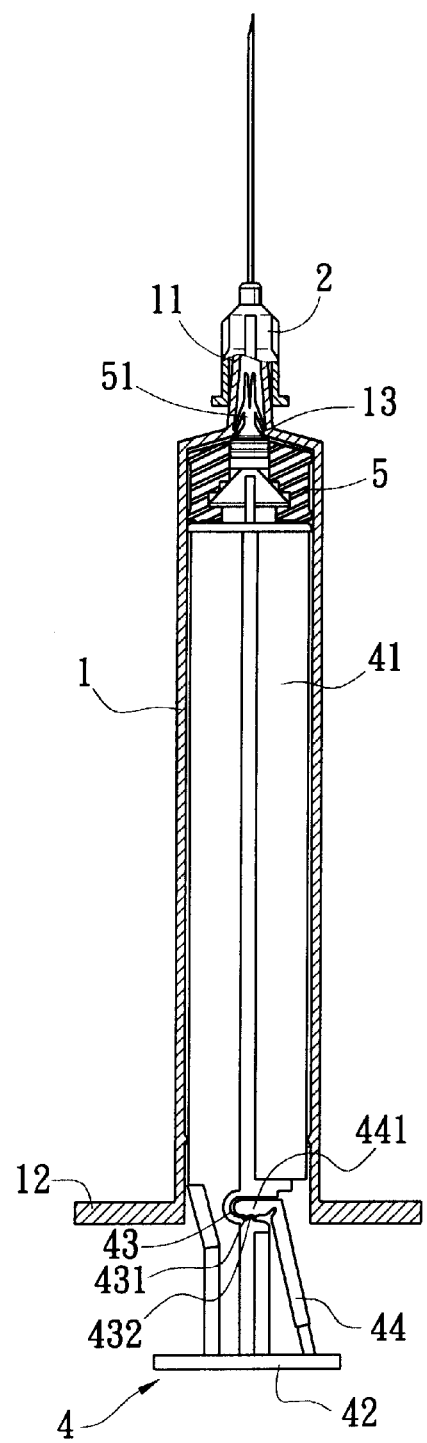
FIG. 3C is also a schematic diagram illustrating the use of the self-destructed syringe of the invention.

FIGS. 3A, 3B and 3C respectively show preferred embodiments of the invention. As shown in the drawings that the utilization steps of the syringes according to the invention are the same as that of conventional syringes. Firstly, the plunger rod 4 is pulled backwards by a hospital specialist to enable pharmaceutical to be sucked into the hollow cylinder 1 due to vacuum formed between the rubber stopper 5 and the hollow fluid chamber 14 for the pharmaceutical preparation. The hospital specialist has to press the safety locking tab 44 into the locking socket 43 to enable the plunger rod 4 to be completely pressed into the hollow cylinder 1 through secure engagement of the head of safety locking tab 441 by a protrusion 432 thereof and a groove 431 of the locking socket 43, when the hospital specialist is ready to inject pharmaceutical into a patient. Consequently, complete pharmaceutical injection through fully pressing the plunger rod 4 into the cylinder 1 enabling the syringe destruction. On the contrary, the syringe can not be destructed if the safety locking tab 44 is not pressed into the locking socket 43 to enable the plunger rod 4 to be completely pushed into the cylinder 1. Therefore, employs the aforesaid safety design to fresh self-destructed syringes can prevent improper huddle of syringes during the processes of assembly or delivery, manual mis-press of syringes from self-destruction and the increase of further waste and syringe defect rates.

Figure 4:
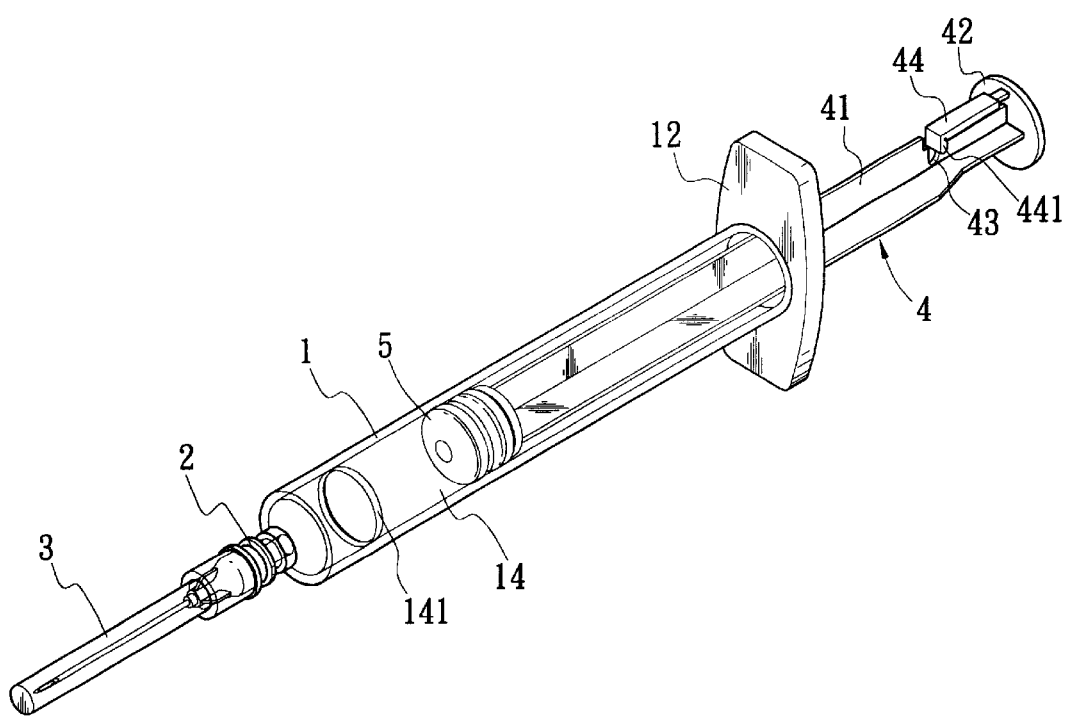
FIG. 4 is another preferred embodiment of a perspective assembly diagram of a self-destructed syringe according to the invention.
Figure 5A:
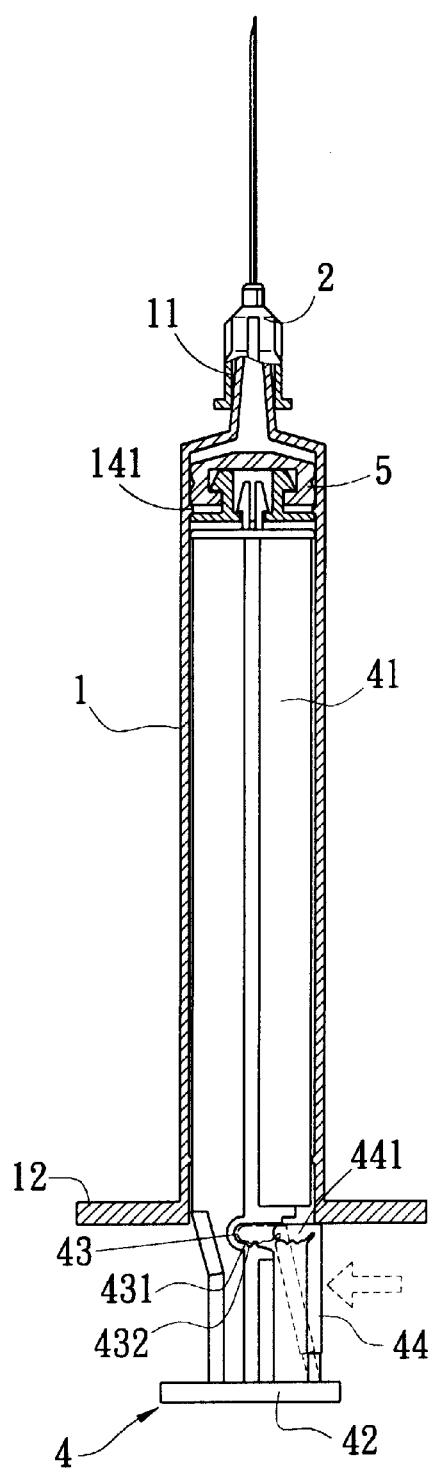
FIG. 5A is a schematic diagram illustrating the use of another preferred embodiment of the self-destructed syringe of the invention.
Figure 5B:
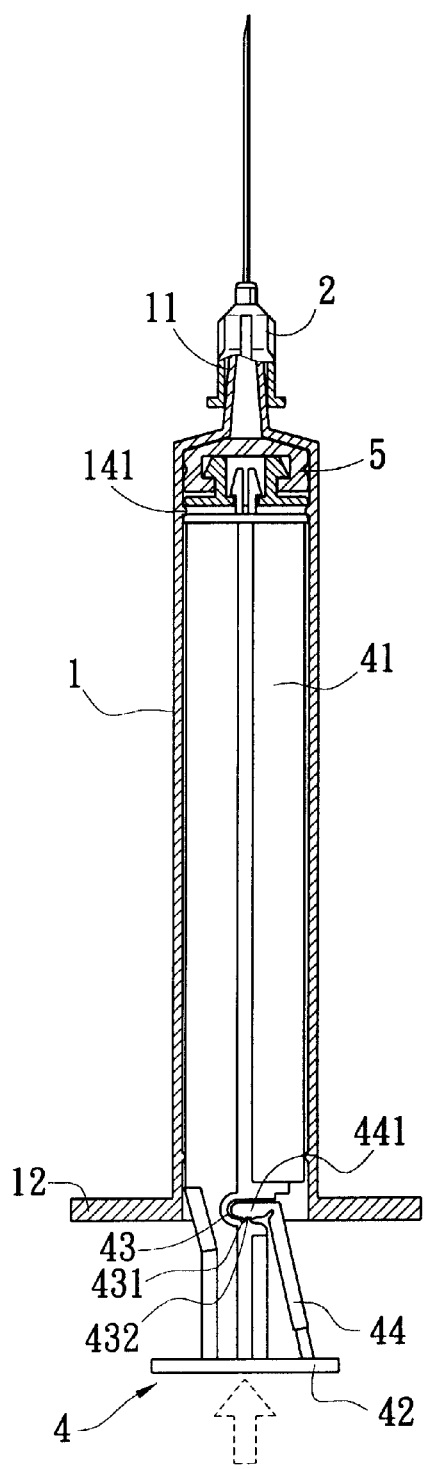
FIG. 5B is also a schematic diagram illustrating the use of another preferred embodiment of the self-destructed syringe of the invention.

Turning now to FIGS. 4, 5A and 5B, all illustrate other diagrams of perspective assembly and utilization representatives that apply to another preferred embodiment of self-destructed syringe. The self-destructed syringe structure also consists of a hollow cylinder 1, a needle 2, a tip protector 3, a plunger rod 4, and a rubber stopper 5. An indented connection head 11 is set at the front end of the hollow cylinder 1 for fixing the needle 2, which is outwardly covered by the tip protector 3. The syringe Sets a ring 141 in the hollow fluid chamber 14 with a distance between the ring and the front end of the hollow fluid chamber 14 the same as the thickness of the rubber stopper 5 enabling the ring 141 to anchor the rubber stopper 5 while the plunger rod 4 is completely pressed into the cylinder, so that the syringe is self-destructed, because that the rubber stopper 5 is permanently engaged with the ring 141 when the plunger rod 4 is pulled backwards.

The invention, a structural safety design for the prevention of mis-pressing plunger into syringe, can be applied to the aforesaid plunger rod 4. The technology and related method are the same as the aforesaid implementation, i.e., the injection steps require a hospital specialist to press the locking tab 44 into the locking socket 43 to enable the plunger rod 4 to be completely pushed into the cylinder 1, when the hospital specialist is ready-to inject pharmaceutical into a patient. Consequently, complete pharmaceutical injection enables the syringe to be self-destructed. On the contrary, the syringe can not be destructed if the locking tab 44 is not pressed into the locking socket 43 to enable the plunger rod 4 to be completely pushed into the cylinder 1.

In view of the foregoing, the aforementioned two self-destructed syringe operations apply the method of completely pressing the plunger rod 4 into the distal(front) end of the hollow cylinder 1 to end up the usage of the syringe. It lives up to the design of single usage principle. Nevertheless, fresh self-destructed syringes easily cause early destruction by the plunger rod 4 being mis-pressed into the hollow cylinder during the processes of syringe assemblies or deliveries, or being improperly unsealed.

It is of course to be understood that the embodiment described herein is merely illustrative of the principles of the invention and that a wide variety of modifications thereto may be effected by persons skilled in the art without departing from the spirit and scope of the invention as set forth in the following claims.

What is claimed is:

1. A structural safety design for the prevention of mis-pressing plunger rod into syringe especially applies to single-used syringe apparatus, which consists of a hollow cylinder, a needle, a tip protector, a plunger rod, and a rubber stopper, which is set at the front end of the plunger rod; the syringe is able to be self-destructed resulting from the engagement mechanism by either a conical front portion at the front end of the rubber stopper or a ring set inside the hollow cylinder when the plunger rod is pressed-inwards; a safety structure to prevent mis-pressing plunger, characterized in that:

a safety structure, consists of a locking socket and a relative safety locking tab set at one sectorial blade of the plunger rod near the end of thumb rest;

a safety locking tab, is in L shaping with a head thereof, the head of the safety locking tab is corresponding to the locking socket;

a locking socket, is set at one sectorial blade corresponding to the head of safety locking tab and forms at least a protrusion and a groove for the engagement;

therefore, prior to the syringe usage, the safety locking tab has to be pressed into the locking socket to enable the head to be securely engaged through both protrusion and groove of the locking socket, so that the plunger rod can be completely pressing into the hollow cylinder for ending up the injection and syringe self-destruction.

2. The structural safety design for the prevention of mis-pressing plunger rod into syringe in accordance with claim 1, wherein the head of the safety locking tab obstructs the flange of the hollow fluid chamber in the hollow cylinder.

3. The structural safety design for the prevention of mis-pressing plunger into syringe in accordance with claim 1, wherein the engagement relationship between the locking socket and the safety locking tab is a anchored structure by a protrusion and a groove.

* * * * *